US00PP18211P2

(12) United States Plant Patent
Miyazaki

(10) Patent No.: US PP18,211 P2
(45) Date of Patent: Nov. 13, 2007

(54) ***PHLOX* PLANT NAMED 'SUNPHLOCORO'**

(50) Latin Name: *Phlox drummondii Hook.*
Varietal Denomination: Sunphlocoro

(75) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/477,024

(22) Filed: Jun. 28, 2006

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent Bell
*Assistant Examiner*—S. B. McCormick-Ewoldt
(74) *Attorney, Agent, or Firm*—Jondle & Associates, P.C.

(57) ABSTRACT

A new *phlox* plant particularly distinguished by abundant, red-purple flowers, abundant branching, excellent tolerance to heat, good tolerance to rain and wind, a vigorous, compact growth habit and continuous flowering from spring to late autumn is disclosed.

1 Drawing Sheet

Genus and species: *Phlox drummondii* Hook.
Variety denomination: 'Sunphlocoro'.

BACKGROUND OF THE NEW PLANT

The present invention comprises a new and distinct cultivar of *phlox,* botanically known as *Phlox drummondii* Hook., and hereinafter referred to by the cultivar name 'Sunphlocoro'. The new cultivar originated from a hybridization made in June 2002 in Higashiomi, Shiga, Japan. The female parent was the proprietary *phlox* plant '2Ph-38a' (unpatented), while the male parent was the proprietary *phlox* plant '2Ph-38b' (unpatented).

The new cultivar was selected from the results of the hybridization in 2004 in Higashiomi, Shiga, Japan and has been asexually reproduced repeatedly by vegetative cuttings in Higashiomi, Shiga, Japan since then. The present invention has been found to retain its distinctive characteristics through successive asexual propagations.

SUMMARY OF THE INVENTION

The following are the most outstanding and distinguishing characteristics of this new cultivar when grown under normal horticultural practices in Higashiomi, Shiga, Japan.

1. Abundant, red-purple flowers;
2. Abundant branching;
3. Vigorous, compact and mounding growth habit;
4. Flowers continuously from Spring to late Autumn;
5. Excellent tolerance to heat; and
6. Good tolerance to rain and wind.

DESCRIPTION OF PHOTOGRAPHS

This new phlox plant is illustrated by the accompanying photographs which show blooms and foliage of the plant in full color, the colors shown being as true as can be reasonably obtained by conventional photographic procedures. The photographs are of a 4-month-old plant grown in a greenhouse in Higashiomi, Shiga, Japan.

DESCRIPTION OF THE NEW CULTIVAR

Figure 1:
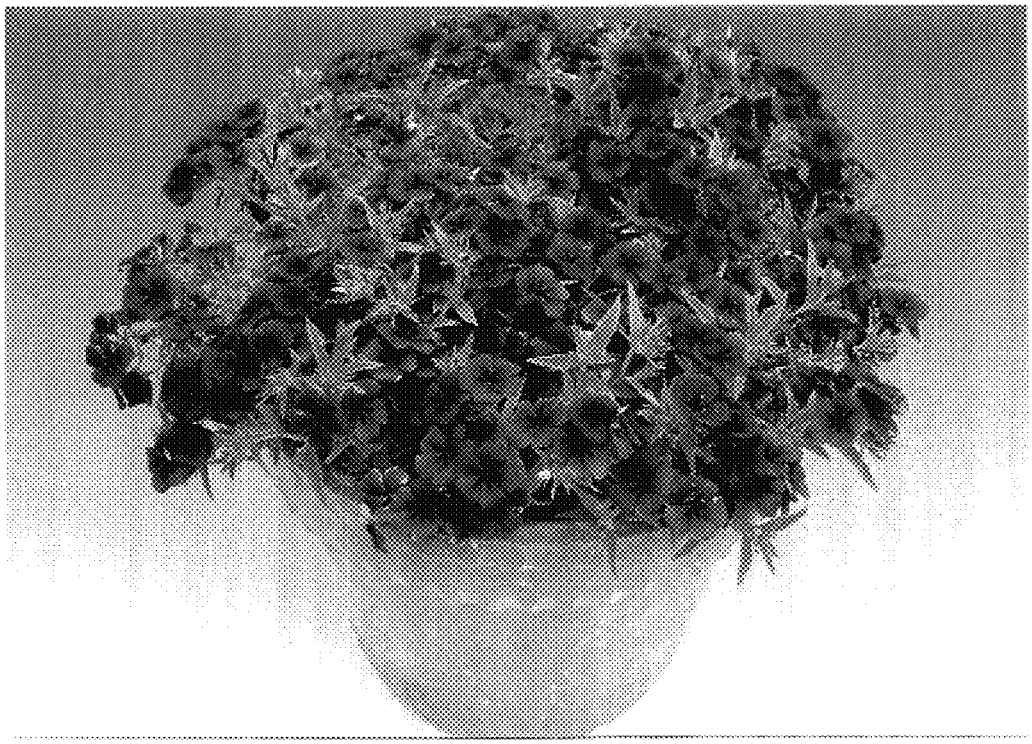
FIG. 1 shows the overall plant habit, including blooms, buds and foliage.
Figure 2:
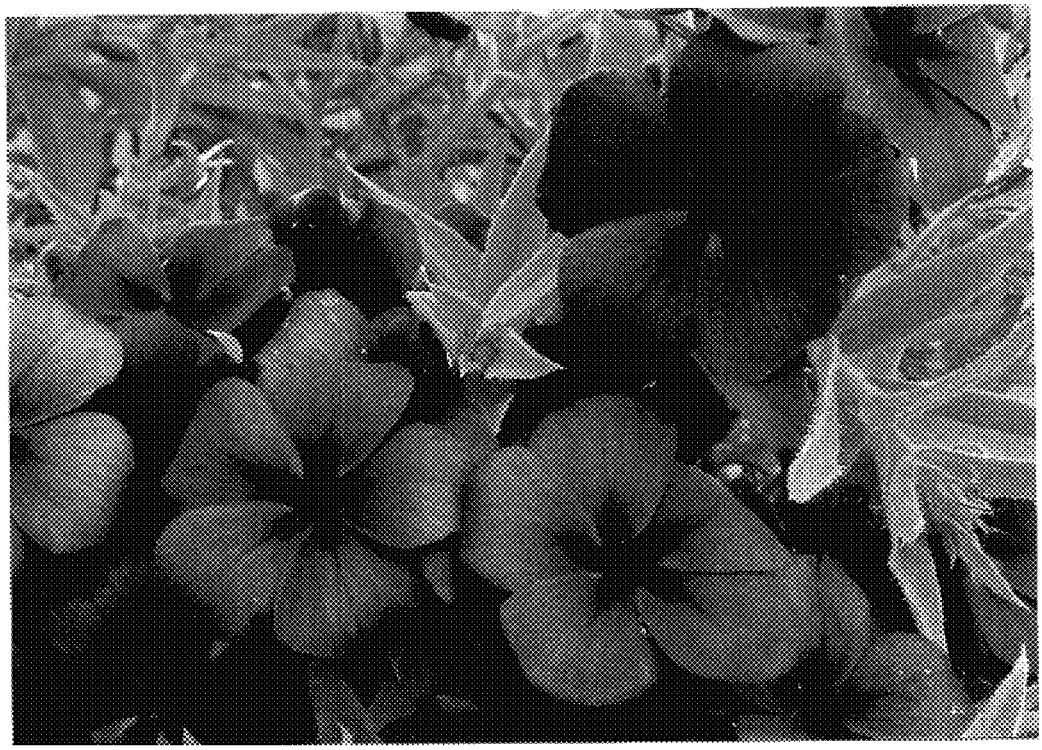
FIG. 2 shows the mature flower.

The following detailed description sets forth the distinctive characteristics of 'Sunphlocoro'. The data which define these characteristics were collected from asexual reproductions carried out in Higashiomi, Shiga, Japan. The plant history was taken on 4-month old plants which were planted as rooted cuttings in 12-cm pots in 2005 and grown in a plastic-covered greenhouse between 16° C. and 20° C. The plants were pinched once in November 2005. Observations were made when the plants were in full flower in March 2006. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Polemoniaceae.
- *Botanical.—Phlox drummondii* Hook.
- *Common name. —Phlox.*

Parentage:
- *Female parent.*—'2Ph-38a', a proprietary purple (RHS N78A) flowered *phlox* plant (unpatented).
- *Male parent.*—'2Ph-38b', proprietary purple (RHS N78A) flowered *phlox* plant (unpatented).

Growth:
- *Form.*—Annual.
- *Habit.*—Mounding, upright, freely branching, vigorous.
- *Height* (*measured from the top of the soil*).—12.6 cm.
- *Diameter or area of spread.*—26.6 cm.
- *Propagation.*—Terminal tips for cutting.
- *Time to produce a finished flowering plant.*—1 month, in April to late October under Japanese conditions, for a 12-cm pot.
- *Keeping quality.*—210 days.

*Outdoor plant performance.*—Use in flower bedding and potting; excellent tolerance to heat; good tolerance to rain and wind.

*Time to initiate and develop roots.*—14 to 21 days at 20° C. to 25° C.

*Time to produce rooted cutting or liner (young plant).*—30 to 60 days at 20° C. to 25° C.

*Root description.*—Ivory or pale brown, fibrous, fine; fleshy, freely-branching.

Branches:

*Number of branches.*—25 lateral branches.

*Length of lateral branches.*—12.0 cm.

*Diameter of lateral branches.*—0.21 cm.

Stems:

*Description.*—Round in cross-section.

*Aspect.*—Upward.

*Color.*—RHS 144B.

*Diameter.*—0.21 cm.

*Stem length.*—12.0 cm.

*Internode length.*—0.9 cm.

*Anthocyanin.*—Absent.

*Texture.*—Pubescent.

Leaves:

*Arrangement.*—Alternate, single leaves.

*Quantity of leaves (per lateral branch).*—17.

*Apex.*—Acute.

*Base.*—Obtuse.

*Color (mature leaves).*—Upper surface: RHS 137B. Lower surface: RHS 138B.

*Color (immature leaves).*—Upper surface: RHS 144A. Lower surface: RHS 143C.

*Margin.*—Entire.

*Size.*—Length: 5.5 cm. Width: 1.4 cm.

*Shape.*—Lanceolate.

*Texture.*—Smooth, pubescence on both sides.

*Venation.*—Type: Reticulate. Color: RHS 145B.

*Petiole.*—Absent.

Flower buds:

*Color.*—RHS 64B.

*Shape.*—Clavate.

*Size.*—Length: 1.59 cm. Diameter: 0.3 cm.

Inflorescence:

*Blooming habit.*—Continuous.

*Inflorescence type.*—Cyme, single flower, self-cleaning.

*Arrangement.*—Terminal and lateral.

*Height.*—4.1 cm.

*Width.*—5.6 cm.

*Aspect.*—Upright to outward.

*Shape.*—Hypocraterimorphous corolla.

*Fragrance.*—Present.

*Flower number (per inflorescence).*—7.

*Quantity of flowers and buds per plant.*—97.

*Flower longevity on plant.*—5 days.

*Peduncle.*—Color: RHS 144B. Length: 0.79 cm. Diameter: 0.1 cm. Texture: Pubescent.

*Pedicel.*—Color: RHS 144B. Length: 0.36 cm. Diameter: 0.1 cm. Texture: Pubescent.

Flowers:

*Size.*—Height (flower depth): 1.8 cm. Diameter: 2.9 cm.

*Corolla.*—Shape: Tube. Color: Inside: RHS 64A. Outside: RHS 70C. Length: 1.3 cm. Diameter: 0.15 cm.

*Petals.*—Arrangement: Single whorl. Shape: Broadly rhombic. Number: 5, fused. Size: Length (from the throat): 1.3 cm. Width: 1.2 cm. Apex: Obtuse. Base: Fused. Margin: Entire. Color (when opening): Upper surface: RHS N66A with RHS N74C eye color. Lower surface: RHS N66D. Color (fully opened): Upper surface: RHS N66A with RHS N74C eye color. Lower surface: RHS N66D. Color fading to: RHS N66C. Petal texture (both surfaces): Smooth.

*Calyx.*—Shape: Star-shaped. Length: 0.91 cm. Diameter: 1.42 cm.

*Sepals.*—Arrangement: Single whorl. Number: 5. Shape: Lanceolate. Apex: Acute. Base: Fused. Margin: Entire. Size: Length: 0.63 cm. Width: 0.14 cm. Color (mature): Upper surface: RHS 137C. Lower surface: RHS 138B. Color (immature): Upper surface: RHS 137C. Lower surface: RHS 138B.

Reproductive organs:

*Stamens.*—Quantity: 5. Anther: Shape: Linear. Length: 0.1 cm. Color: RHS 7B.

*Pollen.*—Amount: Normal. Color: RHS 7A.

*Pistil.*—Quantity: 1. Length: 0.31 cm.

*Style.*—Length: 0.07 cm. Color: RHS 31C.

*Stigma.*—Shape: Stringy, trifid. Color: RHS 8D.

*Ovary color.*—RHS 143B.

Fruit and seed set: Seed production has not been observed.

Disease and insect resistance: No particular resistance or susceptibility to diseases or insects noted to date.

COMPARISON WITH PARENTAL AND COMMERCIAL CULTIVARS

'Sunphlocoro' differs from the female parent '2Ph-38a' (unpatented), by having red-purple (RHS N66A) flowers with red-purple (RHS N74C) eye color, while '2Ph-38a' has purple (RHS N78A) flowers with red-purple (RHS 71A) eye color. Additionally, 'Sunphlocoro' has a smaller plant size than '2Ph-38a'.

'Sunphlocoro' differs from the male parent '2Pha-38b' (unpatented), by having red-purple (RHS N66A) flowers with red-purple (RHS N74C) eye color, while '2Ph-38b' has purple (RHS N78A) flowers with red-purple (RHS 71A) eye color. Additionally, 'Sunphlocoro' has a smaller plant size than '2Ph-38b'.

'Sunphlocoro' is similar to the commercial variety 'Parona Carmine' (unpatented) however, there are differences as listed in Table 1 below:

TABLE 1

Comparison of Characteristics between 'Sunphlocoro' and 'Parona Carmine'

| Characteristic | 'Sunphlocoro' | 'Parona Carmine' |
|---|---|---|
| Plant height | 12.6 cm | 20.0 cm |
| Plant diameter | 26.6 cm | 34.0 cm |
| Leaf color (mature) | Upper surface: RHS 137B<br>Lower surface: RHS 138B | Upper surface: RHS 147B<br>Lower surface: RHS 146C |
| Petal color (fully opened) | Upper surface: RHS N66A with RHS N74C eye<br>Lower surface: RHS N66D | Upper surface: RHS 78B with RHS 70B<br>Lower surface: RHS 65B |
| Sepal length | 0.63 cm | 0.70 cm |
| High temperature tolerance | Excellent | Weak |
| Fertility | Low | High |

I claim:

1. A new and distinct cultivar of *phlox* plant as shown and described herein.

* * * * *